United States Patent [19]
Putnam et al.

[11] Patent Number: 5,586,985
[45] Date of Patent: Dec. 24, 1996

[54] METHOD AND APPARATUS FOR FIXATION OF DISTAL RADIUS FRACTURES

[75] Inventors: Matthew D. Putnam, Minneapolis; David Gesensway, Mendota Heights, both of Minn.

[73] Assignee: Regents of the University of Minnesota, Minneapolis, Minn.

[21] Appl. No.: 329,444

[22] Filed: Oct. 26, 1994

[51] Int. Cl.$^6$ ............................................. A61B 17/56
[52] U.S. Cl. ............................................. 606/69; 606/70
[58] Field of Search ........................ 606/60, 61, 69, 606/70, 71, 72

[56] References Cited

U.S. PATENT DOCUMENTS

| | | | |
|---|---|---|---|
| 3,593,709 | 7/1971 | Halloran | 606/69 |
| 4,565,193 | 1/1986 | Streli | 606/59 |
| 4,782,842 | 11/1988 | Fietti, Jr. | 128/92 |
| 5,006,120 | 4/1991 | Carter | 606/69 |
| 5,108,404 | 4/1992 | Scholten et al. | 606/94 |
| 5,162,039 | 11/1992 | Dahners | 602/23 |
| 5,197,966 | 3/1993 | Sommerkamp | 606/69 |

FOREIGN PATENT DOCUMENTS

WO82/02830 9/1982 WIPO.

OTHER PUBLICATIONS

D. Gesensway et al., "A New Plate for Distal Radius Fractures. Design and Biomechanical Analysis.", *Scientific Exhibit Abstract Form*, 2 pp. (Abstract).

W. A. Zuelzer, "Fixation of Small But Important Bone Fragments with a Hook Plate," *The Journal of Bone and Joint Surgery*, 33–A(2), pp. 430–436 (1951).

Axelrod et al., "Open reduction and internal fixation of comminuted, intraarticular fractures of the distal radius," *The Journal of Hand Surgery*, 15A(1) 1–11 (1990).

Bradway et al., "Open Reduction and Internal Fixation of Displaced, Comminuted Intra-Articular Fractures of the Distal End of the Radius," *The Journal of Bone and Joint Surgery*, 71–A(6) 839–847 (1989).

Missakian et al., "Open reduction and internal fixation for distal radius fractures," *The Journal of Hand Surgery*, 17A(4) 745–755 (1992).

Scheck et al., "Long–Term Follow–up of Treatment of Comminuted Fractures of the Distal End of the Radius by Transfixation with Kirschner Wires and Cast," *The Journal of Bone and Joint Surgery*, 44–A(1) 337–351 (1962).

*Primary Examiner*—Michael Powell Buiz
*Assistant Examiner*—Mark S. Leonardo
*Attorney, Agent, or Firm*—Mueting, Raasch, Gebhardt & Schwappach, P.A.

[57] ABSTRACT

The present invention provides both methods and apparatus for stable internal fixation of distal radius fractures. The apparatus includes a tined plate designed for implantation which is attached to the distal radius with the tines located in fragments of the distal radius and the methods are adapted to placed the plate in the proper position on the dorsal surface of the distal radius.

22 Claims, 4 Drawing Sheets

METHOD AND APPARATUS FOR FIXATION OF DISTAL RADIUS FRACTURES

FIELD OF THE INVENTION

The present invention relates to the field of methods and apparatus for fixating distal radius fractures. More particularly, the present invention relates to methods and apparatus of fixating distal radius fractures using an implantable device and a corresponding guide used to locate the device accurately on the distal radius.

BACKGROUND OF THE INVENTION

One of the most common types of bone fractures in humans is a fracture of the distal radius. Inherent bony instability, soft tissue damage, and frequent associated injuries make distal radius fractures very difficult to treat. Furthermore, the functional outcome is generally directly related to residual deformity, both extra-articular alignment and intra-articular step-off. Closed methods of fixating including casting, pins and plaster, and external fixation have frequently yielded unsatisfactory results. While external fixation can restore and maintain radial length and radial shift, it cannot always restore palmar tilt or reduce articular displacement. Residual radiocarpal incongruities of more than 1 mm have been found to lead to arthritis in 91% of cases at a mean of only 6.7 years after fracture, despite good extra-articular alignment using known methods. Additionally, fixator related complications are not insignificant and the cost and duration of treatment are typically high.

Limited open reduction techniques, combined with iliac crest bone grafting and external fixation have produced good early results for simple intra-articular fractures with large fragments. Results in achieving anatomic reduction and early rehabilitation while eliminating or shortening the period of external fixation have been promising with formal open reduction and internal fixation. Furthermore, the value of immediate mobilization of the injured joints is clear, but the currently available options for internal fixation frequently fail to achieve sufficient stability in the radial bone to allow early motion with its accompanying benefits.

One device developed for internal fixation is commonly referred to as a T-plate. The T-plate was designed to buttress simple partial articular fractures of the distal radius (dorsal and volar Barton's; AO types B2 and B3) against an intact cortex and has worked well in this setting. However, for more unstable situations, particularly A3, C1, C2 & C3 by AO classification, the standard T-plate has failed with plate bending, breaking and/or screw loosening, with a consequent loss of reduction. As a result, the standard T-plate either cannot be used or must often be combined with external fixator or cast neutralization to avoid loss of reduction due to screw loosening, screw pullout, or plate bending. As a result, the benefits obtained from early mobilization cannot be achieved.

Furthermore, T-plates may not be useful in situations revolving highly comminuted fractures in which screw purchase is not available to sufficiently attach the T-plate.

U.S. Pat. No. 5,006,120 to Carter discloses one device for fixating distal radius fractures. The device includes a plate which is secured to the dorsal surface of the distal radius and a plurality of blades which are attached to the plate using threaded fasteners. Became of the separate nature of the blades and plate, movement of the blades relative to the plate and, therefore, fracture fragments, is difficult to control. In addition, the connection between the blades and plate provides an area of stress concentration which may cause catastrophic failure, such as shearing of the screw used to connect the blade and plate.

An additional disadvantage of the Carter device is that implantation requires removal of all or a portion of the cortex beneath the holes in the plate to obtain a low profile. As a result, each screw used to attach the Carter device typically does not engage more than one cortex (with a total of three cortices engaged proximal to the typical fracture pattern), thereby limiting the strength of attachment of the plate to the radius and raising the potential for screw pullout during use.

U.S. Pat. No. 5,197,966 to Sommerkamp discloses a device for fixating distal radius fractures. The device includes a plate designed for placement on the distal radiodorsal surface of the radius and includes blades, or tines, which extend from the central region of the plate for insertion into the radius. The blades are not positioned to specifically support the scaphoid and lunate fossae, and, as a result, typically do not offer the necessary level of support to the separate joint surfaces and to the subchondral bone needed to allow early mobilization.

A further disadvantage of the Sommerkamp device is that the plate will interfere with function of the first dorsal compartment tendons as well as the brachial radialis tendons. These interferences may hinder the mobilization which assists in healing.

Other attempts at internal fixation of unstable distal radius fractures include the use of small wires and mini fragment plates which have been used as internal suture to help maintain anatomic reduction. Typically, however, these methods often require an external fixator or cast for neutralization of forces across the wrist, once again eliminating the opportunity to achieve the benefits provided by early mobilization.

SUMMARY OF THE INVENTION

The present invention provides both methods and apparatus for stable internal fixation of distal radius fractures.

In one aspect, the present invention provides a tined plate designed for implantation which is attached to the distal radius with the tines located in fragments of the distal radius.

In another aspect, the present invention includes both the plate as described above as well as a guide designed to allow accurate placement of the plate and its associated tines on the dorsal surface of the distal radius. The preferred guide includes openings corresponding to the tines in the plate as well as openings to receive wires which are used to temporarily fix the guide in place to both determine if its position is correct, as well as to maintain its position during formation of pilot openings in the distal radius to receive the tines of the plate.

Both the plate and guide are shaped to substantially conform to the profile of the dorsal surface of the distal radius. By attaching the plate to the dorsal surface of the distal radius, tendons and ligaments are not requires to pass over the plate and the plate is, instead, covered with soft tissue after implantation.

The present invention also provides a method of fixating distal radius fractures using the plate described above. In the most preferred method, the present invention also comprises the method of using the guide described above to form the necessary openings in the distal radius to allow placement of the tines in the plate.

One advantage of the plate according to the present invention is its ability to fix unstable distal radius fractures with sufficient stability to allow immediate motion. In biomechanical terms, the plate and bone combination provides sufficient yield strength to maintain elastic behavior under anticipated physiologic postoperative loads. When compared to the known T-plate, the plate manufactured according to the present invention provides an average yield strength which is 2 to 2.5 times that of the T-plate.

Furthermore, the plate according to the present invention presents a low profile when implanted while maintaining strength and providing for up to six or more sites of screw engagement with cortices proximal to the typical fracture. Obtaining a maximum number of threaded interfaces with cortices is important to minimize the risk of screw pullout and/or loosening.

Another advantage of the plate is that it includes tines which, when properly positioned, independently support both the scaphoid and lunate fossae.

Yet another advantage of the plate is its unitary construction, which avoids threaded interfaces and other joints between the plate and tines which may be susceptible to failure.

Yet a further advantage of the preset invention is that it provides an apparatus and method for the fixation of highly comminuted fractures in which adequate screw purchase is not available at the distal portion of the radius. Instead, the plate according to the present invention can be attached with wires at its distal end. Even though screws are not provided distally, the strength of the plate/bone construct is sufficient to allow for early mobility to enhance healing.

These and other features and advantages of the methods and apparatus according to the present invention will become apparent upon reading the detailed description below as well as with reference to the drawings.

DETAILED DESCRIPTION OF THE PREFERRED EMBODIMENTS AND METHODS

Figure 1:
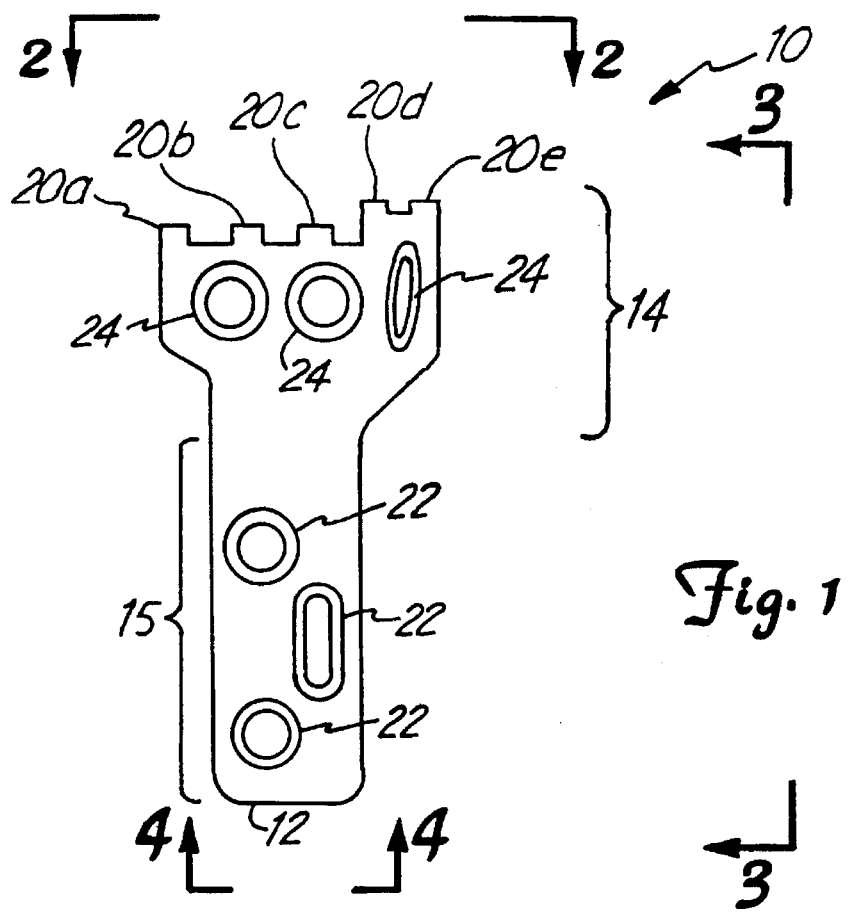
FIG. 1 is a plan view of the posterior surface of one plate according to the present invention.

FIG. 1 is a plan view taken from the posterior side of the plate 10. For purposes of reference, this view is referred to as the posterior view because, when implanted, this is the surface of the plate which will be visible from the posterior perspective. Generally, the plate 10 provides a three-dimensional structure which directly carries loads normally carried by the radius. By forming the plate 10 in three dimensions, i.e., with an arcuate proximal section 15 and a bent distal section 14, the plate 10 offers enhanced rigidity even when the plate thickness is reduced.

Figure 4:
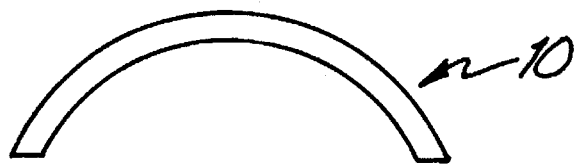
FIG. 4 is an enlarged view of the proximal end of the plate of FIG. 1 taken along line 4—4, with the background deleted for clarity.

The plate 10 includes a proximal end 12 which is preferably a portion of arcuately-formed flat or machined plate as best shown in the cross section of FIG. 4. Preferably, the shape of this proximal portion 15 of plate 10 substantially matches the profile of the portion of the radius on which it will be located. It will, however, be understood that this portion of the plate could be bent and formed during the implantation process as variations in the shape of the radius may be present.

Screw holes 22 are provided in the radial shaft portion of device 10. As shown in FIG. 1, holes 22 are preferably not colinear, but are rather radially spaced about the circumference of the radius to provide improved strength in plate 10 as well as improved rotational stability of plate 10 when attached to a radius. Holes 22 are preferably oversized to allow screws to be angulated and countersunk full thickness for a low profile. Furthermore, one or more of the holes 22 could be provided as slots to provide more flexibility in relative plate length after initial screw placement.

Figure 2:
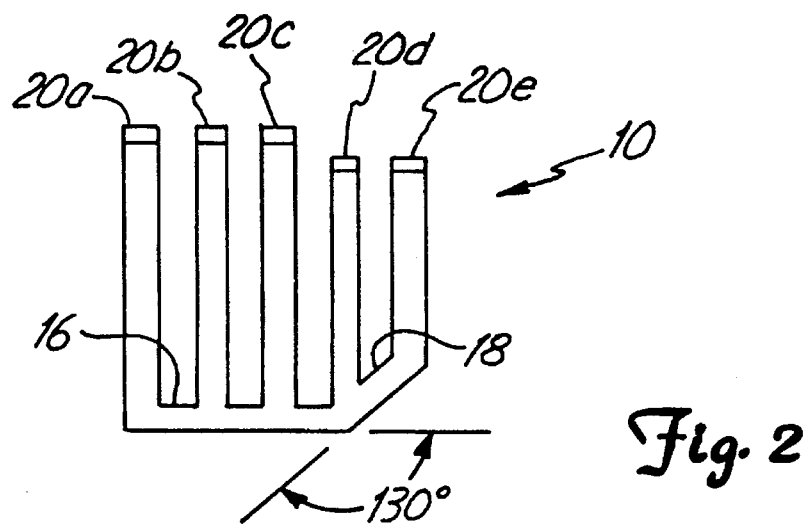
FIG. 2 is an end view taken along line 2—2 of the plate according to FIG. 1, with the background deleted for clarity.
Figure 3:
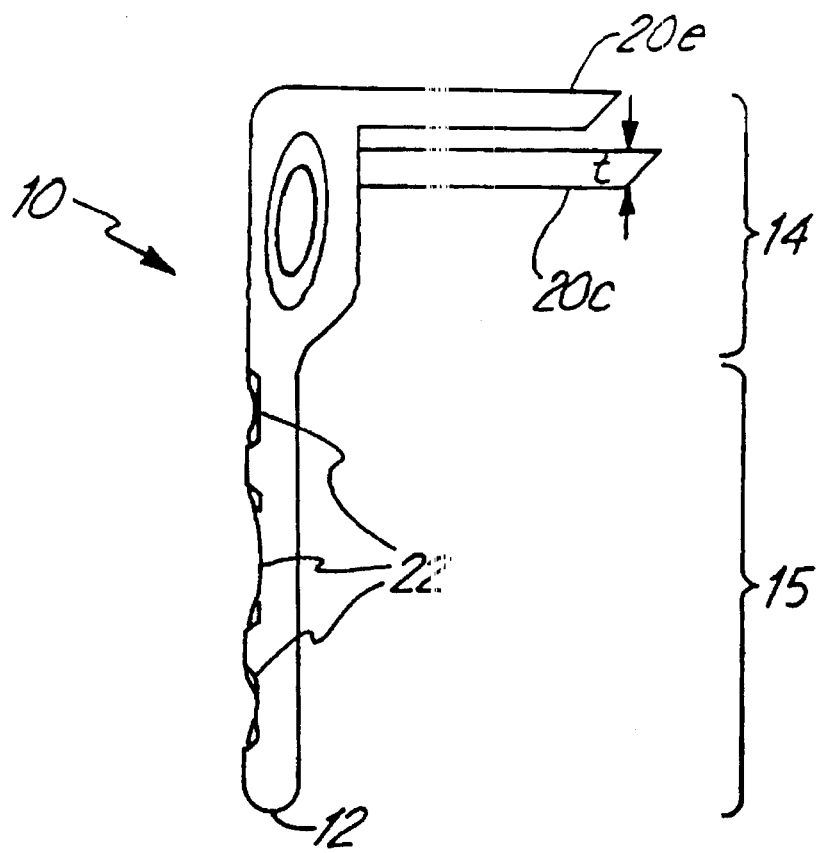
FIG. 3 is a side view of the plate according to FIG. 1 taken along line 3—3.

The distal portion 14 of plate 10 is best seen with reference to FIGS. 1, 2 and 3. As shown there, portion 14 includes a first surface 16 and a second surface 18. In the preferred embodiment, both surfaces 16 and 18 are preferably substantially planar. Also in the preferred embodiment, surface 16 and surface 18 intersect at an included angle of approximately 130°. That angle is chosen to substantially match the dorsal profile of a radius at its distal end.

Tines, generally referred to as 20, extend from the distal end of plate 10 at substantially right angles to the longitudinal axis of the plate. Also, as shown best in FIG. 2, the tines are substantially parallel to each other and are substantially normal to the first surface 16. Tines 20d and 20e which extend from the second surface 18 are also preferably normal to first surface 16 as seen in FIGS. 2 and 3.

Tines 20a through 20c are positioned to support the lunate fossa while tines 20d and 20e are placed to support the scaphoid fossa. The longitudinal offset of the scaphoid tines 20d and 20e from the lunate tines 20a through 20c improves rotational control provided by plate 10. In use, the tines 20 are to be placed in predrilled pilot holes just beneath the subchondral plate and are designed to carry loads directly from the subchondral plate through the plate 10 to the proximal radius, thus preventing shortening of the radius during the healing process. The plate is not designed to produce fragment compression, but is rather designed to be an internal neutralization device to allow healing while providing for mobility in the joint.

Although the preferred plate 10 includes three tines 20a–c to support the lunate fossa and two tines 20d and 20e to support the scaphoid fossa, it will be understood that two or more tines could be provided to support the lunate fossa and, likewise, that two or more tines could be provided to support the scaphoid fossa. A minimum of two tines to support each fossa is desirable to prevent rotation of the fragments relative to the longitudinal axis of the radius.

The distal portion 14 of plate 10 also includes at least one hole 24 sized to receive screws. In the preferred embodiment, three holes 24 provided and are preferably oversized to allow the screws to be angulated and countersunk full thickness for a low profile. One of the holes 24 formed through the surface 18 of distal portion 14 is preferably provided as a slot to receive a screw which can be moved longitudinally along slot as desired. Furthermore, the holes 24 are preferably sized to have a diameter of 4.5 mm and countersunk full thickness to a 6 mm head to allow for angulation. Those holes which are elongated allow for more angulation as desired by a practitioner.

In the preferred plate, there are no holes in the metaphyseal region of the plate to increase its strength across the fracture region.

One preferred plate 10 is 1.5 mm thick and has a width of 12.0 mm at the proximal end 12. At the distal portion 24 the plate is preferably 24 mm wide, and includes five tines 20 which have a square cross-section of 2 mm per side. The overall length of plate 10 varies transverse to its longitudinal axis to accommodate the varying distances at which the lunate and scaphoid fossae are located. Tines 20d and 20e which preferably support the scaphoid fossae are located approximately 55 mm from the proximal end 12 of plate 10. In the preferred guide 10, the tines 20a–c are located approximately 3 mm closer to the proximal end 12 than are tines 20d and 20e to improve rotational control and accommodate the positioning of scaphoid fossa. It will be understood, however, that these dimensions may be modified to accommodate anatomical differences between patients in different age and/or size groups.

The preferred material for plate 10 is stainless steel, most preferably 316L. It will be understood that other materials could be used in place of the preferred stainless steel, provided the strength of the device was not significantly adversely affected.

One process of manufacturing the plate 10 is to machine the plate 10 and tines 20 from a solid piece of material. By machining the device from a solid block, the thickness, t, of the tines 20 can differ from the thickness of the plate 10 to enhance stiffness of the device. In addition, because the tines 20 are machined at the correct orientation with respect to the surfaces 16 and 18, the tines 20 need not be bent or formed during manufacture which could introduce residual stresses into the plate/tine interface and result in lower toughness and ductility due to work hardening.

In the preferred device described above, the proximal and distal portions of the plate 10 are 1.5 mm thick, while the tines 20 have a square cross-section of 2.0 mm on each side. As a result, the profile of the proximal and distal portions, 14 and 15, of the plate 10 is lower when implanted while the tines 20 provide substantial support to the subchondral plate. It will be understood that the shape and relative dimensions of the plate and tines can be varied as needed and/or desired.

In one process where the device is machined from a solid piece of metal, surfaces 16 and 18 are machined as substantially coplanar along with proximal section 15 of plate 10. After machining, the openings 22 and 24 are formed through the proximal and distal portions of the plate 10. The arcuate portion of the proximal section 15 and the radial flair (comprising surface 18) of the distal portion of plate 10 could be press-formed after machining. If the radial flair is press-formed after machining, the initial angle of tines 20d and 20e differs from the orientation of tines 20a–c. After press-forming, however, all of the tines 20 are preferably substantially parallel to each other and normal to surface 16.

Alternatively, the entire device, including the radial flair and arcuate portions could be machined rather than press-formed. In addition, the tines would also be machined in the correct orientation. This is the preferred method of manufacture as it introduces no residual stresses or work hardening into the device.

An alternate process of manufacturing a plate 10 in which the plate 10 is as thick as the tines 20 is to cut or form the plate 10 and tines 20 from a single piece of flat stock material. After the plate has been formed, openings 22 and 24 are drilled and countersunk and the ends of the tines 20 are beveled to facilitate their insertion into the radius. The arcuate portion of the plate 10 is then press-formed and the radial flair, which comprises second surface 18 as seen in FIG. 2 is then bent to the desired angle with respect to surface 16. After the radial flair has been formed, tines 20 are then bent into position.

Any of the methods described above, or other methods not described above, in which the tines 20 are formed completely integral and unitary with the remainder of plate 10 could be used to manufacture devices according to the present invention. In that way, the interface between tines 20 and plate 10 should not present an area which could be the source of failure in devices in which tines or pins are provided as separate articles which must be attached by some means, such as threading, to a separate plate.

Figure 5:
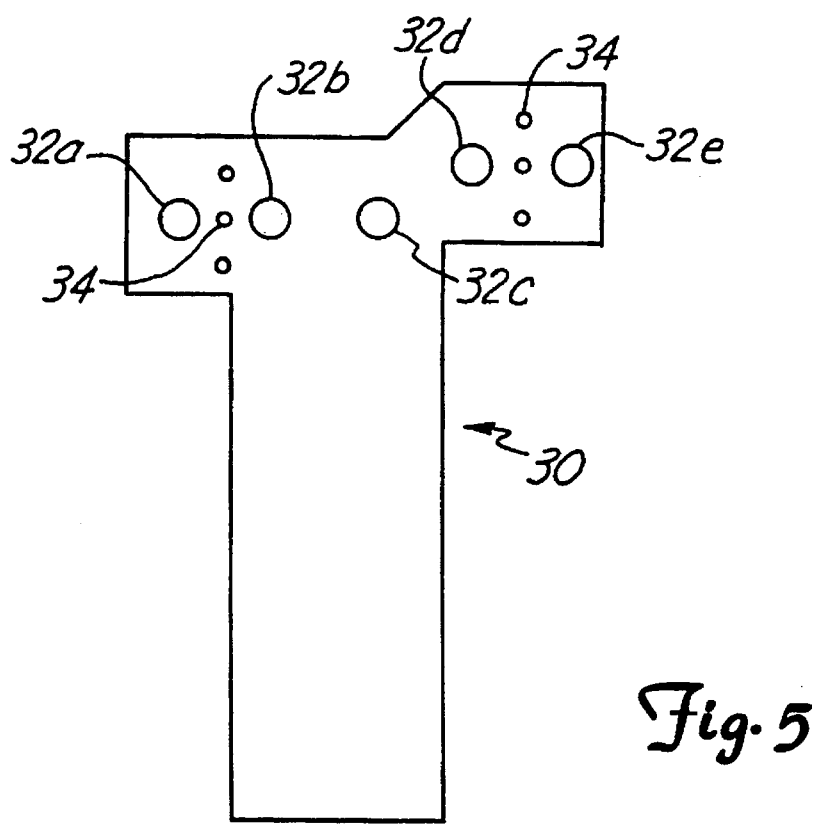
FIG. 5 is a posterior view of one guide according to the present invention for use in combination with the plate of FIG. 1.
Figure 6:
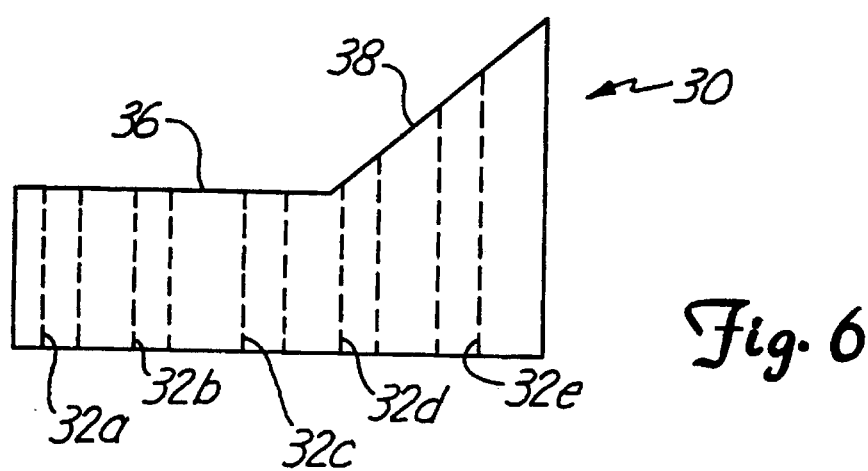
FIG. 6 is an end view taken along line 6—6 of the guide of FIG. 5 with the openings through the guide shown as hidden lines.

Turning now to FIGS. 5 and 6, the preferred guide for use with plate 10 is shown and will be described below.

Guide 30 includes a first surface 36 and a second surface 38 which intersect an included angle of approximately 130° or any other angle which matches the included angle formed by surfaces 16 and 18 in the preferred plate 10. As a result, the guide 30 can be placed on the dorsal surface of the distal radius in a position mimicking that desired for plate 10.

A plurality of holes, generally referred to by reference number 32, are provided in the guide 30. Placement of holes 32 correspond to the placement of tines 20 in the preferred plate 10. It is preferred that the distal portion of the guide 30 (including the surfaces 36 and 38) have a thickness sufficient to adequately control the orientation of a drill bit inserted through the openings 32. In the preferred embodiment, the portions of guide 30 containing openings 32 is at least 10 mm.

As a result, when guide 30 is in its proper position on the distal radius, openings 32 can be used to guide a drill bit or other means of forming pilot holes in the distal radius to facilitate insertion of tines 20 in preferred plate 10. Holes 32a–c direct a drill bit to positions proximate the lunate fossa while holes 32d and 32e direct a drill bit towards positions proximate the scaphoid fossa.

In the preferred embodiment, tines 20 have a 2 mm square cross section. As a result, it is preferred that holes 32 and drill guide 30 provide for the passage of a 2 mm diameter drill bit. Other dimensions may be used as desired and/or necessary.

The preferred guide 30 also includes a series of wire openings 34 located appropriately with respect to the openings 32. Wire openings 34 are designed to accommodate wires partially inserted into the bone to fix the position of guide 30, as will be described below in more detail regarding methods of using the guide 30 and plate 10 according to the present invention. In the preferred embodiment, a set of three wire openings 34 is located between the openings 32a and 32b (arrayed longitudinally) and a second set of wire openings 34 is located between openings 32d and 32e (also arrayed longitudinally).

Guide 30 is preferably formed of materials which are less radiographically dense than metallic wires inserted into wire openings 34 in guide 30 to temporarily fix the guide in position. Once in position, the area is imaged, preferably using known image intensification equipment. Became the relationship between the wire openings 34 (and the wires inserted into them) is known, the practitioner can determine the position of openings 32 with respect to the radius. As a result, the location of pilot holes which would be formed in the radius by a drill bit inserted through openings 32 in guide 30 is also known. If necessary, the guide 30 can be repositioned and the area imaged again until the guide 30 and are associated openings 32 properly positioned.

In a preferred embodiment, guide 30 is preferably formed of a polycarbonate material in which the openings 32 are lined with stainless steel bushings or some other material which is not easily removed by a drill bit inserted through openings 32. It will be understood that the guide 30 could also be manufactured of a variety of other materials such as aluminum, titanium, plastics, etc. Resistance of the openings 32 to wear (provided by stainless steel bushings in openings 32 of the preferred embodiment) is important to ensure accurate, repeatable alignment of pilot holes formed in the distal radius using the guide 30. An additional advantage of lining openings 32 with a radio-dense material such as stainless steel is the ability to view the openings 32 in the image intensification process.

Figure 7:
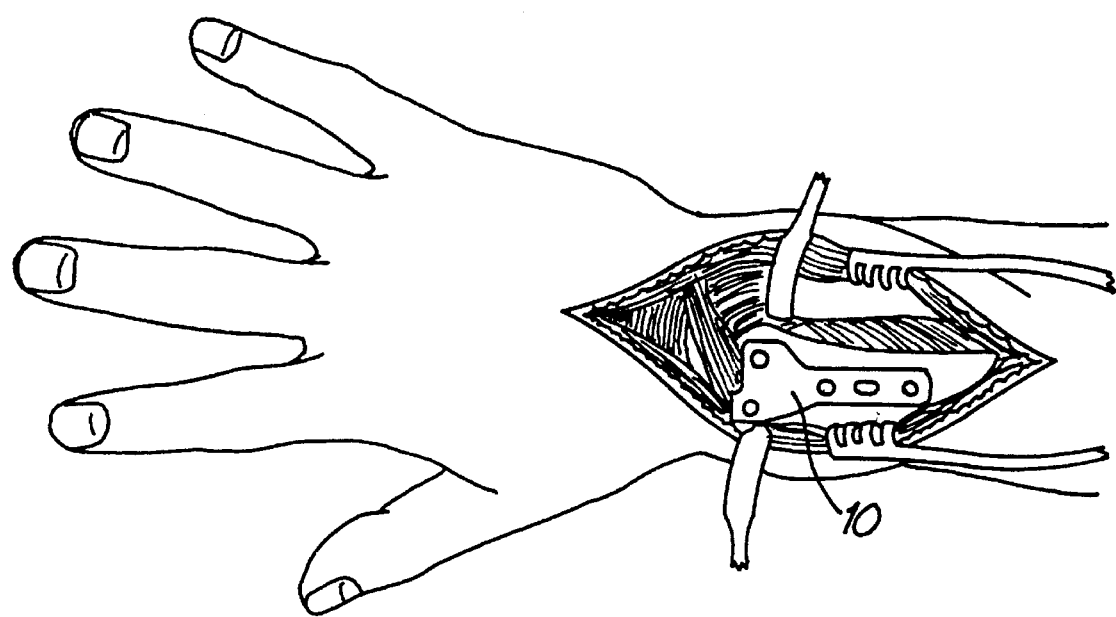
FIG. 7 is a schematic diagram of a method of attaching a plate according to the present invention to the dorsal surface of the distal radius.

The plate according to the present invention is designed to be applied clinically via a dorsal (or combined dorsal and volar) approach to the distal radius and the radiocarpal joint. Open reduction is facilitated by distraction with a 2-pin external fixator and direct visualization of the articular surface to apply a plate 10 as depicted in FIG. 7. Temporary K-wire fixation is used as needed, and anatomic alignment is confirmed with image intensification equipment.

Prior to placement of a guide 30 according to the present invention, Lister's tubercle must be removed to allow for seating the guide 30 and, subsequently, the plate 10. After Lister's tubercle is removed, a guide 30 is positioned on the dorsal surface of the distal radius. It is temporarily fixed in position by a plurality of wires inserted through wire openings 34 as described above. These wires penetrate the surface of the distal radius to temporarily fix the position of the guide 30 on the radius.

Positioning is then checked using a posterior to anterior view and a lateral view of the guide 30 and radius using image intensification equipment. Because the preferred guide 30 is formed of a material which is less radio-dense than the wires used to temporarily fix the guide 30 in position, the wires can be viewed in the images and, therefore, the position of opening 32 can be determined. If necessary, the guide 30 can be repositioned to ensure alignment of openings 32 with the appropriate areas of the subchondral plate.

Once the position of the guide 30 is correct, pilot holes are drilled in the distal radius using openings 32 formed through guide 30. The guide 30 is then removed and plate 10 is then positioned proximate the distal radius and finger pressure is used to seat tines 20 in the respective holes formed using guide 30. After the tines 20 have been seated, 4.0 mm cancellous screws are placed distally through the holes 24 formed in plate 10. After placement of the screws in the distally placed holes 24, the 3.5 mm cortical screws are tapped and placed proximally through openings 22. After fixation of plate 10 on the distal radius, the metaphyseal region can be bone grafted as needed, and PMMA or similar substances to augment distal fixation can be used as needed.

Alternately, the plate 10 can be attached without distal screws in openings 24 formed proximate the distal end of plate 10. It in situations such as highly comminuted fractures or others where distal screw purchase is not available in which the present invention offers the ability to fixate distal radius fractures in a manner which allows for early mobilization and the resulting enhancement of healing. Known devices and methods do not offer this ability.

In those instances where distal screw purchase is not available of desired, fixation of the plate 10 is supplemented with two longitudinal, oblique 0.045 inch K-wires (Clancey method). As yet a further alternative, the plate 10 can be fixed without distal screws but supplemented with a dorsal tension 24-gauge wire over the distal end of the plate 10. Importantly, this non-distally screw fixated method is laboratory proven to offer more rigidity and higher yield strength that distally screw-fixated existing T-plates (even though such a method of fixation would not be possible became of the lack of screw purchase).

Where distal screw purchase is available, however, it is preferred to use screws at the distal end of plate 10 as testing has shown that fixation of plate 10 with distally placed screws provide further increases in the mean strength, or failure load, for fractures using plates 10 according to the present invention.

After the plate 10 has been attached as described above, the external fixator is loosened and fracture stability is checked. If the fracture is stable, which is most often possible, the external fixator is then removed. If secure fixation is uncertain, an external fixation device would be used for an appropriate interval, usually four weeks.

The closure procedure further includes covering the plate with available joint capsule and periosteal tissue along with repairing the extensor tendon sheath and retinaculum prior to closure of the site.

Postoperative management of patients in which the plate according to the present invention is used includes a splint for 1 to 2 weeks to promote soft tissue healing, after which a removable protective splint is used to allow for wrist motion during the rehabilitation process.

Although the methods and apparatus according to the present invention have been described in detail above with respect to particular preferred embodiments and methods, it will be evidenced that various and further modifications are possible without departing from the spirit and scope of the present invention as defined by the claims.

We claim:

1. A plate for stable fixation of distal radius fractures comprising:

a) an elongated plate adapted for attachment to the dorsal surface of the radius, the plate having a proximal end and a distal end, wherein the distal end comprises first and second substantially planar surfaces, the first and second surfaces forming an included angle adapted to substantially match the curvature of the dorsal surface of the distal end of the radius, and further wherein the proximal end of the plate is curved such that the proximal end is adapted to substantially match the profile of the near distal portion of the radius;

b) a plurality of tines extending from the distal end of the plate, wherein each tine is completely integral and unitary with the plate, and further wherein each tine is oriented substantially normal to the first surface such that when the plate is located on a radius, each of the plurality of tines is adapted to extend into the radius; and c) a plurality of openings extending through the plate adapted to receive fasteners to fasten the plate to the radius.

2. A plate according to claim 1, wherein at least one of the plurality of tines extends from the first surface of the distal end of the plate and at least one of the plurality of tines extends from the second surface of the distal end of the plate, and further wherein the first surface is located such that each tine extending from the first surface of the distal end of the plate is adapted to extend through the radius proximate the lunate fossa and further wherein the second surface is located such that each tine extending from the second surface of the distal end of the plate is adapted to extend through the radius proximate the scaphoid fossa.

3. A plate according to claim 1, wherein the included angle formed by the first and second substantially planar surfaces is about 130 degrees.

4. A plate according to claim 1, wherein at least one of the plurality of tines has a thickness, measured in a direction from the proximal end to the distal end of the plate, greater than the thickness of the plate.

5. A plate according to claim 1, wherein at least one of the tines is located further from the proximal end of the plate than the remaining tines.

6. A plate according to claim 2, wherein two or more of the plurality of tines extend from the first surface of the distal end of the plate and two or more of the plurality of tines extend from the second surface of the distal end of the plate.

7. A plate for stable fixation of distal radius fractures comprising:

a) an elongated plate adapted for attachment to the dorsal surface of the radius, the plate having a proximal end and a distal end, wherein the distal end comprises first and second substantially planar surfaces, the first and second surfaces forming an included angle of about 130 degrees, thereby adapting the distal end of the plate to substantially match the curvature of the dorsal surface of the distal end of the radius, and further wherein the proximal end of the plate is curved such that the proximal end of the plate is adapted to substantially match the profile of the near distal surface of the radius;

b) a plurality of tines extending from the distal end of the plate, wherein each tine is completely integral and unitary with the plate and at least one of the tines is located further from the proximal end of the plate than the remaining tines, and further wherein at least one of the plurality of tines has a thickness, measured in a direction from the proximal end to the distal end of the plate, greater than the thickness of the plate, and yet further wherein each tine is oriented substantially normal to the first substantially planar surface, and yet still further wherein at least one of the plurality of tines extends from the first surface of the distal end of the plate and at least one of the plurality of tines extends from the second surface of the distal end of the plate, and further wherein each tine extending from the first surface of the distal end of the plate is adapted to extend into the radius proximate the lunate fossa and each tine extending from the second surface of the distal end of the plate is adapted to extend into the radius proximate the scaphoid fossa; and c) a plurality of openings extending through the plate adapted to receive fasteners to fasten the plate to the radius.

8. A combination for the stable fixation of distal radius fractures comprising:

a) an implantable plate adapted for attachment to the dorsal surface of the radius comprising:

1) an elongated plate having a proximal end and a distal end, wherein the distal end comprises first and second substantially planar plate surfaces, the first and second plate surfaces forming an included angle adapted to substantially match the curvature of the dorsal surface of the distal end of the radius, and further wherein the proximal end of the plate is curved such that the proximal end of the plate is adapted to substantially match the profile of the near distal portion of the radius, 2) a plurality of tines extending from the distal end of the plate, wherein each tine is completely integral and unitary with the plate, and further wherein each tine is oriented substantially normal to the first plate surface such that when the plate is located on a radius each of the plurality of tines is adapted to extend into the radius, and 3) a plurality of openings extending through the plate adapted to receive fasteners to fasten the plate to the radius; and b) a guide for accurate placement of a plurality of bores in the radius, each of the plurality of bores corresponding to one of the plurality of tines extending from the plate, the guide comprising:

1) an elongated body adapted for placement on the dorsal surface of the radius, the body having a proximal end and a distal end, wherein the distal end comprises first and second substantially planar guide surfaces, the first and second guide surfaces forming an included angle adapted to substantially match the curvature of the dorsal surface of the distal end of the radius, 2) a plurality of guide openings extending through the distal end of the body, wherein each guide opening is oriented substantially normal to the first guide surface such that when the guide is located on the dorsal surface of the distal end of a radius each of the plurality of guide openings is axially aligned with each of the plurality of tines.

9. A combination according to claim 8, wherein at least one of the plurality of tines extends from the first plate surface of the distal end of the plate and at least one of the plurality of tines extends from the second plate surface of the distal end of the plate, and further wherein each tine extending from the first surface of the distal end of the plate is adapted to extend through the radius proximate the lunate fossa and further wherein each tine extending from the second surface of the distal end of the plate is adapted to extend through the radius proximate the scaphoid fossa.

10. A combination according to claim 8, wherein the included angle formed between the first and second substantially planar plate surfaces and the included angle formed between the first and second substantially planar guide surfaces are each about 130 degrees.

11. A combination according to claim 8, wherein at least one of the tines is located further from the proximal end of the plate than the remaining tines.

12. A combination according to claim 8, wherein the guide further comprises means for temporarily attaching the guide to the distal radius.

13. A combination according to claim 12, wherein the means comprises a plurality of wire openings formed through the guide which are adapted to receive wires that are adapted to be inserted into the radius to temporarily attach the guide to the distal radius.

14. A plate according to claim 9, wherein two or more of the plurality of tines extend from the first plate surface of the distal end of the plate and two or more of the plurality of tines extend from the second plate surface of the distal end of the plate.

15. A method for fixating a distal radius fracture comprising the steps of:
   a) positioning a guide over the dorsal surface of the distal end of the radius, the guide comprising:
      1) an elongated body adapted for placement on the dorsal surface of the radius, the body having a proximal end and a distal end, wherein the distal end comprises first and second substantially planar guide surfaces, the first and second guide surfaces forming an included angle adapted to substantially match the curvature of the dorsal surface of the distal end of the radius,
      2) a plurality of guide openings extending through the distal end of the body, wherein each guide opening is oriented substantially normal to the first guide surface;
   b) forming a plurality of pilot holes in the distal end of the radius, each of the pilot holes formed in axial alignment with a corresponding guide opening, at least one of the pilot holes located proximate the lunate fossa and at least one of the pilot holes formed proximate the scaphoid fossa;
   c) removing the guide from the radius;
   d) locating an implantable device on the distal end of the radius, the device comprising:
      1) an elongated plate adapted for attachment to the dorsal surface of the radius, the plate having a proximal end and a distal end, wherein the distal end comprises first and second substantially planar surfaces, the first and second surfaces forming an included angle adapted to substantially match the curvature of the dorsal surface of the distal end of the radius, and further wherein the proximal end of the plate is curved such that the proximal end is adapted to substantially match the profile of the near distal portion of the radius,
      2) a plurality of tines extending from the distal end of the plate, wherein each tine is completely integral and unitary with the plate, and further wherein each tine is oriented substantially normal to the first surface such that when the plate is located on the dorsal surface of the distal end of a radius each of the plurality of tines extends into a corresponding one of the plurality of pilot holes in the radius, and
      3) a plurality of openings extending through the plate adapted to receive fasteners to fasten the plate to the radius; and
   e) attaching the plate to the radius with a plurality of threaded fasteners extending through the plurality of openings in the plate and into the radius.

16. A method according to claim 15, further comprising the step of attaching the distal portion of the plate to the radius using wire supplementation.

17. A method according to claim 16, wherein the wire supplementation comprises placing at least two longitudinal oblique wires over the plate using the Clancey method.

18. A method according to claim 16, wherein the wire supplementation further comprises a dorsal tension wire placed over the distal portion of the plate.

19. A method according to claim 16, further comprising the step of checking the position of the guide on the radius before the step of forming the plurality of pilot holes to ensure that at least one of the plurality of guide openings is proximate the lunate fossa and that at least one of the plurality of guide openings is proximate the scaphoid fossa.

20. A method according to claim 15, further comprising the step of temporarily attaching the guide to the distal radius before forming the plurality of pilot holes.

21. A method according to claim 20, wherein the step of temporarily attaching the guide further comprises placing wires in wire openings formed through the guide, the wires extending into the distal radius to stabilize the guide in position.

22. A method according to claim 15, wherein the step of forming a plurality of pilot holes in the distal end of the radius further comprises forming two or more pilot holes located proximate the lunate fossa and two or more pilot holes proximate the scaphoid fossa.

* * * * *

UNITED STATES PATENT AND TRADEMARK OFFICE
CERTIFICATE OF CORRECTION

PATENT NO.: 5,586,985
DATED: December 24, 1996
INVENTOR(S): Matthew D. Putnam et al.

It is certified that error appears in the above-identified patent and that said Letters Patent is hereby corrected as shown below:

Col. 6, line 66, delete "Became the" and insert --Because the--; and

Col. 12, line 21, delete "claim 16" and insert --claim 15--.

Signed and Sealed this

Thirteenth Day of October 1998

*Attest:*

BRUCE LEHMAN

*Attesting Officer*     *Commissioner of Patents and Trademarks*